US011633447B2

(12) United States Patent
Won et al.

(10) Patent No.: US 11,633,447 B2
(45) Date of Patent: Apr. 25, 2023

(54) PHARMACEUTICAL COMPOSITION AND FUNCTIONAL HEALTH FOOD FOR PREVENTING OR TREATING MACULAR DEGENERATION

(71) Applicant: LEMONEX INC., Seoul (KR)

(72) Inventors: Cheol Hee Won, Seoul (KR); Jun Kim, Seoul (KR)

(73) Assignee: LEMONEX INC., Seoul (KR)

( * ) Notice: Subject to any disclaimer, the term of this patent is extended or adjusted under 35 U.S.C. 154(b) by 213 days.

(21) Appl. No.: 17/258,312

(22) PCT Filed: Jul. 9, 2019

(86) PCT No.: PCT/KR2019/008418
§ 371 (c)(1),
(2) Date: Jan. 6, 2021

(87) PCT Pub. No.: WO2020/013571
PCT Pub. Date: Jan. 16, 2020

(65) Prior Publication Data
US 2021/0228670 A1    Jul. 29, 2021

(30) Foreign Application Priority Data
Jul. 9, 2018    (KR) .................. 10-2018-0079302

(51) Int. Cl.
| | |
|---|---|
| *A61K 36/61* | (2006.01) |
| *A23L 33/105* | (2016.01) |
| *A61P 27/02* | (2006.01) |
| *A61K 9/00* | (2006.01) |

(52) U.S. Cl.
CPC ............ *A61K 36/61* (2013.01); *A23L 33/105* (2016.08); *A61K 9/0053* (2013.01); *A61P 27/02* (2018.01); *A61K 2236/333* (2013.01); *A61K 2236/51* (2013.01)

(58) Field of Classification Search
None
See application file for complete search history.

(56) References Cited

U.S. PATENT DOCUMENTS

2009/0252796 A1* 10/2009 Mazed ................... A61K 36/54
424/490

FOREIGN PATENT DOCUMENTS

| CN | 104824675 A | 8/2015 |
|---|---|---|
| CN | 107412465 A | 12/2017 |
| JP | 61-37731 A | 2/1986 |
| JP | 10-291935 A | 11/1998 |
| JP | 2009-184992 A | 8/2009 |
| KR | 10-2010-0114347 A | 10/2010 |
| KR | 10-2011-0090536 A | 8/2011 |
| KR | 10-2016-0056268 A | 5/2016 |
| KR | 10-2017-0043689 A | 4/2017 |
| WO | WO 2014/116013 A1 | 7/2014 |

OTHER PUBLICATIONS

International Search Report for PCT/KR2019/008418 dated Oct. 7, 2019.
15 guava leaf benefits, side effects, and tea, How to Make Tea http://catalk.kr/food/guava-leaves.html, 2017 (English machine translation is submitted herewith.).
Parul Thapar, "Health Nutrients for Healthy Eyes", Science Reporter, pp. 30-32, Aug. 2015.
Sang Geun Roh et al., "Antidiabetic Synergistic Effects of Medicinal Plant Extract Mixtures on db/db Mice", Journal of Life Science, vol. 21. No. 2. pp. 165-175, 2011.
Sang Geun Roh et al., "Antidiabetic Effects of Leaves Extracts of *Psidium guajava* L. and *Lagerstroemia speciosa* L. in STZ-induced Rats", Journal of Life Science, vol. 19. No. 1. pp. 40-45, 2009.
European Search Report for EP 19835142.1 dated Apr. 7, 2022 from European patent office in a counterpart European patent application.
Zhong Wei et al., "Screening of *Lagerstroemia* specious Leaves Constituents Hypoglycemic Activity", Journal of Food Science and Biotechnology, vol. 25. No. 3. May 2006 (English translation of abstract is in the first page.).
Zhan Qin, Wang Yan et al., "Studies on the Chemical Constituents of Petroleum Ether Extract of *Lagerstroemia speciosa* (Linn.) Pers Leaves" Lishizhen Medicine and Materia Medica Research 2009 vol. 20 No. 9 (English Abstract is included in the first page.).
He Ling et al., "Protection of Ursolic Acid to Oxygen-Induced Retinopathy in Rats" Recent Advances in Ophthalmology vol. 33 No. 10 Oct. 2013 (English Abstract is included in the first page.).

* cited by examiner

*Primary Examiner* — Russell G Fiebig
(74) *Attorney, Agent, or Firm* — The PL Law Group, PLLC

(57) ABSTRACT

A composition according to an embodiment of the present disclosure includes a banaba leaf extract, a guava leaf extract or a mixture thereof. The composition inhibits photooxidation of A2E due to blue light, inhibits a death of retinal pigment epithelial cells induced by blue light, and inhibits a damage to outer nuclear layers of visual cells in an animal model with blue light-induced macular degeneration, and thus can be beneficially used as a composition for preventing or treating macular degeneration and as a health functional food for preventing or alleviating macular degeneration.

9 Claims, 6 Drawing Sheets

PHARMACEUTICAL COMPOSITION AND FUNCTIONAL HEALTH FOOD FOR PREVENTING OR TREATING MACULAR DEGENERATION

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2019/008418, filed Jul. 9, 2019 which claims priority to the benefit of Korean Patent Application No. 10-2018-0079302 filed in the Korean Intellectual Property Office on Jul. 9, 2018, the entire contents of which are incorporated herein by reference.

TECHNICAL FIELD

The present invention relates to a pharmaceutical composition for preventing or treating macular degeneration, and a health functional food for preventing or alleviating macular degeneration.

BACKGROUND ART

The nerve tissue located in a central portion of the retina is called macular. This portion is a very dense area of visual cells, which forms an image of an object, serves to give central vision and contributes to clarity and accuracy of the field of view. Degeneration may occur due to aging, damage caused by UV or blue light, genetic factors, basal diseases (diabetes, dyslipidemia, hypercholesterolemia), toxicity and inflammation, hence causing dysfunction in eyesight. This is called macular degeneration. Macular degeneration is one of the major causes of blindness, along with cataracts, glaucoma and diabetic retinopathy. When degeneration occurs in the macula, the central vision is initially damaged to cause blurred or crushed vision, which leads to a serious disease of blindness if it gets worse.

Macular degeneration may be divided into two types: dry (non-exudative) macular degeneration and wet (exudative) macular degeneration. Dry macular degeneration accounts for about 90% of an entire patient suffering from macular degeneration, and is characterized that the macular tissue is contracted or thinned due to accumulation of wastes named drusen between retinal pigment epithelium and Bruch's membrane. On the other hand, wet macular degeneration accounts for about 10% of the entire patient, and refers to severe vision loss caused by abnormal formation of neovascular vessels due to no supply of blood and nutrients to the macula, and rupture thereof to leak blood or mucus into the macula. Early signs of the dry macular degeneration are asymptomatic or, even if they are symptomatic, are considered as presbyopia, that is, the eyesight of the aged. Therefore, these are often ignored. However, if progress of the dry macular degeneration is not suppressed or treated, loss of vision due to persistent retinal damage may occur. Further, this may lead to wet macular degeneration and thus to blindness. Therefore, it is important to prevent dry macular degeneration in the early stage.

The major mechanism of dry macular degeneration is not exactly known but will be influenced by various factors. It is assumed that a major cause may be loss of normal functions of retinal pigment epithelial cells. Retinal epithelial cells generally play a role of phagocytosis and degradation of outer segments of photoreceptor cells and are also involved in stress regulation and homeostasis in the retina. Photoreceptor cells and retinal epithelial cells undergo a visual circuit process, whereby by-product pigment A2E (N-retinyl-N-retinylidene ethanolamine) and lipofuscin, a mixture of lipids and proteins, are formed. Retinal pigment epithelial cells may accumulate A2E and lipofuscin through phagocytosis, of which A2E is accumulated without being easily excreted in the cell. A high concentration of A2E is a major cause in regard to death of retinal pigment epithelial cells. In addition, A2E is photooxidized to UV or blue light even at a low concentration, and is converted into epoxide forms such as peroxy-A2E and furano-A2E. Highly reactive epoxide form of A2E causes inflammatory reaction as well as oxidative stress, and modifies protein activity of mitochondria to induce apoptosis. As a result, loss of normal retinal pigment epithelial cells leads to secondary death of photoreceptor cells. In particular, the macula with highly concentrated photoreceptor cells is severely damaged, thereby causing macular degeneration.

Meanwhile, guava (*Psidium guajava*) is a plant belonging to Myrtaceae, mainly distributed in the subtropical region and generates many branches in a length of 3 to 7 m. Guavas are widely distributed in the tropics and subtropical regions including India, southern Mexico and South America. Guava leaves are high in polyphenols and are known to be effective in diabetes, cardiovascular disease, cancer and infectious diseases.

Banaba (*Lagerstroemia speciosa*) is a deciduous tropical plant belonging to the Buddha family, of which roots and leaves are used for food. Banaba is widely distributed in the tropics and subtropical regions including India, southern China, Myanmar and the Philippines. The leaves are elliptical and 18 cm long and 6 cm wide, and contain a large amount of corosolic acid. Banaba leaves are known to be effective in diabetes, obesity, infectious diseases, cancer, etc., in particular, have antioxidation and anti-inflammatory activities.

Therefore, while developing a therapeutic agent for macular degeneration using natural materials that have been used for a long time and are safe for human, the present inventors have found that guava leaf and banaba leaf extracts inhibit photooxidation of A2E due to blue light, inhibit death of blue light-induced retinal pigment epithelial cells, and further prevent a damage to outer nuclear layers of visual cells in an animal model with blue light-induced macular degeneration, and therefore, the present invention has been completed on the basis of the above finding.

SUMMARY

An object of the present invention is to provide a pharmaceutical composition for preventing or treating macular degeneration, and a health functional food for preventing or alleviating macular degeneration.

To achieve the above objects, the following technical solutions are adopted in the present invention.

1. A pharmaceutical composition for preventing or treating macular degeneration, including a banaba leaf extract or a guava leaf extract.

2. The pharmaceutical composition according to the above 1, wherein an extraction solvent for the extract includes at least one of water and $C_1$ to $C_4$ alcohol.

3. The pharmaceutical composition according to the above 1, wherein an extraction solvent for the extract includes at least one of methanol and ethanol.

4. The pharmaceutical composition according to the above 1, wherein the composition includes the banaba leaf extract and the guava leaf extract.

5. A health functional food for preventing or alleviating macular degeneration, including a banaba leaf extract or a guava leaf extract.

6. The health functional food according to the above 5, wherein an extraction solvent for the extract includes at least one of water and $C_1$ to $C_4$ alcohol.

7. The health functional food according to the above 5, wherein an extraction solvent for the extract includes at least one of methanol and ethanol.

8. The health functional food according to the above 5, wherein the health functional food includes the banaba leaf extract and the guava leaf extract.

The extract of the present invention inhibits photooxidation of A2E due to blue light, inhibits a death of retinal pigment epithelial cells induced by blue light, and prevents a damage to the outer nuclear layers of visual cells in an animal model with blue light-induced macular degeneration, and therefore, can be beneficially used as a composition for preventing or treating macular degeneration or a health functional food for preventing or alleviating macular degeneration.

DETAILED DESCRIPTION

Figure 1:
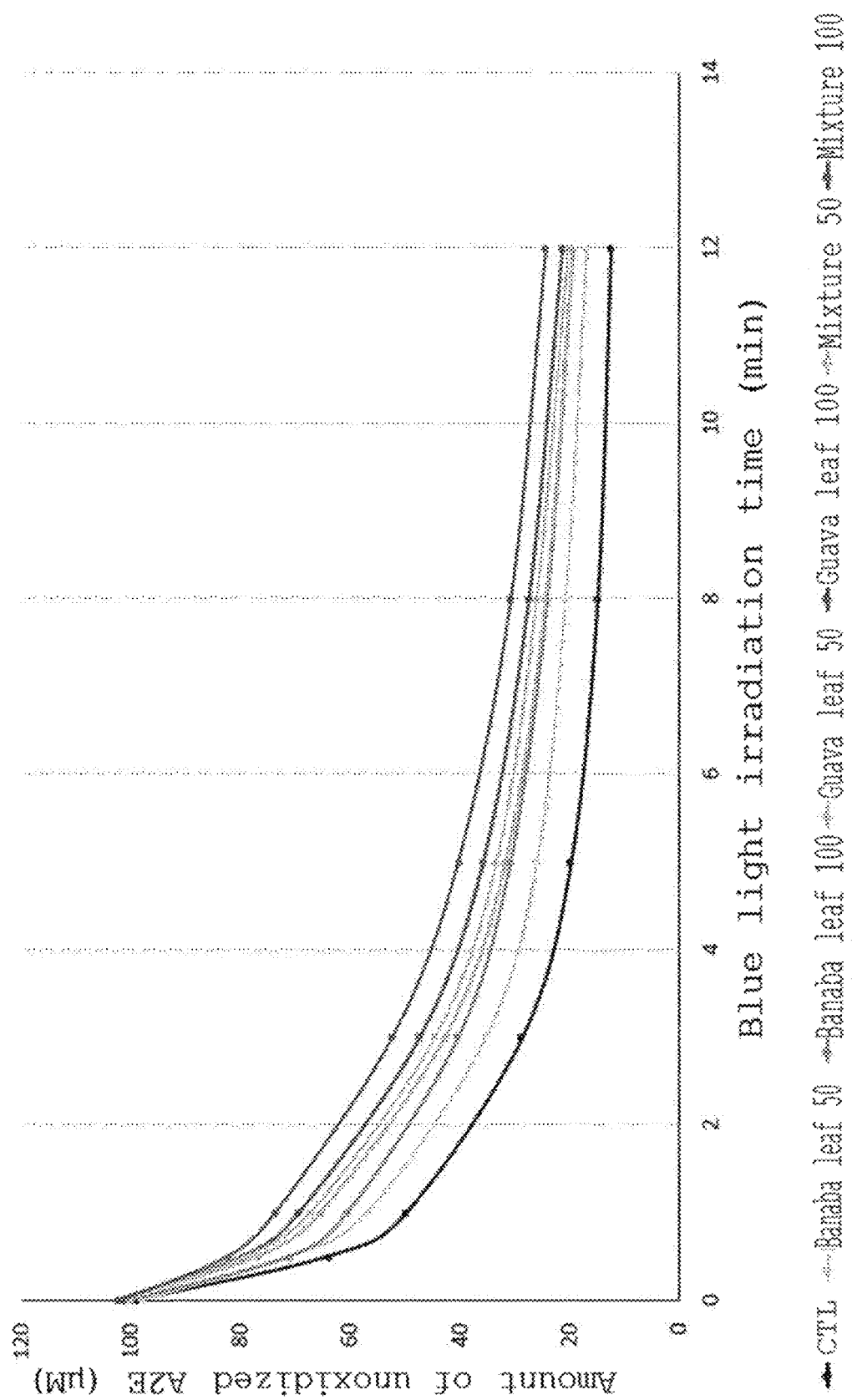
FIG. 1 is a diagram illustrating effects of inhibiting A2E photooxidation due to blue light by guava leaves, banaba leaves and a mixture thereof by time (minutes).

Hereinafter, the present invention will be described in detail.

The present invention provides a pharmaceutical composition and health functional food for preventing or treating macular degeneration, which include a banaba leaf extract or guava leaf extract.

The macular degeneration includes both dry macular degeneration and wet macular degeneration.

A method of extracting banaba leaves or guava leaves is not particularly limited, and may include any extraction method commonly used in the art. Examples of the extraction method include hot water extraction, ultrasonic extraction, filtration, reflux extraction, and the like, and extraction may be performed by any one of the above methods alone or in combination of two or more thereof, but it is not limited thereto.

The solvent used for extracting the banaba leaves or guava leaves is not particularly limited, and may include solvents commonly used in the art. Water-soluble solvents used for extraction may include, for example, at least one selected from the group consisting of water, and $C_1$ to $C_4$ alcohols, or a mixture of two or more different solvents.

The banaba leaf or guava leaf extract may be present in an amount of, for example, 10 to 90 parts by weight ("wt. parts"), and preferably, 25 to 75 wt. parts in the composition.

The banaba leaf or guava leaf extract shows excellent effect on prevention or treatment of macular degeneration. More specifically, the banaba leaf or guava leaf extract inhibits photooxidation of A2E due to blue light, inhibits a death of retinal pigment epithelial cells induced by blue light, and prevents a damage to outer nuclear layers of visual cells in an animal model with blue light-induced macular degeneration. Therefore, these extracts may be used to prevent or treat macular degeneration.

The composition may include a banaba leaf extract or guava leaf extract alone but, in an aspect of achieving synergistic effects in prevention or treatment of macular degeneration, preferably includes a mixture thereof in an appropriate ratio relative to each other.

A weight ratio of each of the banaba leaf extract and guava leaf extract in the mixture may be, for example, 1:⅓ to 3, preferably 1:0.5 to 2.

In the prophylactic or pharmaceutical composition including the extract described above, the term "treatment" refers to any action to improve or advantageously change symptoms of macular degeneration through administration of the extract or a composition containing the same. Those skilled in the art to which the present invention pertains can understand exact criteria of diseases to which the extract or composition of the present invention is effective, with reference to data presented by the Korean Medical Association, etc., and therefore, would determine degrees of alleviation, improvement and/or treatment of the diseases.

In addition, the term "prevention" refers to any action to suppress or delay onset of macular degeneration though administration of the extract or a composition containing the same. It will be apparent to those skilled in the art that the extract or the composition of the present invention having therapeutic effects on macular degeneration can prevent such diseases when taken during or before appearance of initial symptoms.

The compositions of the present invention may be administered simultaneously or sequentially and a mixture of the extracts may be administered alone or in combination with other pharmaceutically active ingredients for treatment of macular degeneration.

The composition of the present invention may further include excipients such as suitable carriers, diluents, preservatives, stabilizers, wetting agents, emulsifiers, solubilizers, sweeteners, colorants, osmotic pressure regulators, antioxidants and the like, which are commonly used in the manufacture of pharmaceutical compositions. Specifically, lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxy benzoate, propylhydroxy benzoate, talc, magnesium, stearate, mineral oil, etc. may be exemplified.

A method of administering the composition according to the present invention may be easily selected on the basis of formulations, and the composition may be administered to mammals such as domestic animals and human through various routes. For instance, the composition may be formulated in a form of powders, tablets, pills, granules, sugarcoated tablets, hard or soft capsules, liquids, emulsions, suspensions, syrups, elixirs, external preparations, suppositories, sterile injectable solutions, and so on, and used for oral or parenteral administration, in particular, preferably, oral administration.

Solid formulations for oral administration include tablets, pills, powders, granules, capsules, etc., and such solid formulations may be prepared by adding at least one excipient, for example, starch, calcium carbonate, sucrose or lactose, gelatin, etc. to the composition of the present invention. In addition to simple excipients, lubricants such as magnesium stearate, talc, etc. are also used. Liquid formulations for oral administration include suspensions, solutions, emulsions, syrups, etc., and may include various excipients such as wetting agents, sweeteners, fragrances, and preservatives, in addition to commonly used simple diluents such as water and liquid paraffin.

Formulations for parenteral administration include, for example, sterile aqueous solutions, non-aqueous solvents, suspensions, emulsions, lyophilized preparations and suppositories. As the non-aqueous solvent and the suspension solvent, propylene glycol, polyethylene glycol, vegetable oil such as olive oil, injectable ester such as ethyl oleate, and the like may be used. As a base of the suppository, witepsol, macrogol, tween 61, cacao butter, laurin butter, glycerol, gelatin and the like may be used.

Further, a pharmaceutical composition including the composition of the present invention may be preferably formulated using any of appropriate methods known in the art or methods disclosed in Remington's Pharmaceutical Science, Mack Publishing Company, Easton, Pa.

A dosage of the composition according the present invention may vary depending on body weight, age, gender and health condition of a patient, diet, administration time, administration method, excretion rate and severity of disease, etc., and may be altered according to different conditions. A frequency of administration may be once or several times a day within the desired range, and an administration period is not particularly limited. In addition, the composition of the present invention may be usually ingested by adding the composition to any food, other than oral administration as it is. At this time, the content of the composition to be added may be determined according to the purpose, and generally in a range of 0.01 to 90 wt. parts based on a total food weight.

Forms and types of the health functional food containing the above extract for preventing or treating macular degeneration are not particularly limited, but may be formulated and processed in a form of tablets, capsules, powders, granules, liquids, pills and the like.

The health functional food of the present invention refers to foods manufactured and processed using raw materials or ingredients having functional properties useful for the human body according to Act No. 6727 of the Health Functional Foods Act, and may mean a food for intake in order to obtain beneficial effects for health use such as control of nutrients for a structure and function of the human body or physiological action.

The health functional food of the present invention may include any conventional food additive. Herein, suitability of the health functional food as a food additive is judged on the basis of standards and criteria of corresponding items according to the General Regulations of the Food Additives and General Test Methods approved by the Food and Drug Administration, unless otherwise specified.

The items listed in the General Regulations of the Food Additives include, for example: chemical compounds such as ketones, glycine, calcium citrate, nicotinic acid and cinnamon acid; natural additives such as dark blue pigment, licorice extract, crystalline cellulose, high color pigment and guar gum; and mixed preparations such as sodium L-glutamate preparations, noodle-added alkaline chemicals, preservative preparations, and tar coloring preparations, and the like, but it is not limited thereto.

For example, a health functional food in the form of tablets may be produced by mixing peptide with an excipient, a binder, a disintegrant and other additives to prepare a mixture, granulating the mixture in any conventional manner, and then, compression molding the same along with addition of a lubricant or directly compression molding the mixture. Further, the health functional food in the form of tablets may contain a flavor enhancer, or the like as necessary.

Among health functional foods in the form of capsules, a hard capsule formulation may be produced by filling a typical hard capsule with a mixture of peptides and additives such as excipients, and a soft capsule formulation may be produced by filling a capsule base such as gelatin with a mixture of peptides and additives such as excipients. The soft capsule formulation may further contain a plasticizer such as glycerin or sorbitol, a colorant, a preservative, and the like as necessary.

A health functional food in the form of pills may be produced by molding a mixture of peptide and excipients, binders, disintegrants, etc. according to any known method and, if necessary, may be enveloped with white sugar or other enveloping agents. Alternatively, the surface of the food may be coated with specific materials such as starch, talc and the like.

A health functional food in the form of granules may be produced by granulating a mixture of peptide and excipients, binders, disintegrants, etc. according to a known method and, if necessary, may contain a flavoring agent, a flavor enhancer, and the like as necessary.

The health functional food may be beverages, meat, chocolate, foods, confectionery, pizza, ramen, other noodles, gums, candy, ice cream, alcoholic beverages, vitamin complexes and dietary supplements.

Hereinafter, the present invention will be described in more detail by means of examples.

Example 1. Preparation of Each Extract, and Mixture Thereof

1. Preparation of Guava Leaf Extract

Dried guava leaf powders (100%, Indian) were purchased from Phytotech Extracts Pvt Ltd. The dried powders were subjected to extraction in distilled water at 100° C. at a rate of 100 g/1 L for 2 hours. The extracted concentrate was filtered, concentrated using a rotary concentrator, and then lyophilized to prepare a guava leaf extract of the present invention.

2. Preparation of Banaba Leaf Extract

Dried banaba leaf powders (100%, Indonesia) were purchased from Sambo food. The dried powders were subjected to extraction with alcohol at a rate of 100 g/1 L. The extracted concentrate was filtered, concentrated using a rotary concentrator, and then lyophilized to prepare a banaba leaf extract of the present invention.

3. Preparation of a Mixture of the Above Extracts

The guava leaf extract and banaba leaf extract were mixed at a weight ratio of 1:1 to obtain a mixture.

Example 2. Analysis of A2E Photooxidation Inhibitory Ability of Each Extract or Mixture Thereof to Blue Light 1. Analysis of A2E Photooxidation Inhibitory Ability of Each Extract or a Mixture Thereof to Blue Light (1) Experimental Method After adding 100 μL of A2E (100 μM final concentration) to a 96-well plate, a control, the guava leaf extract, the banaba leaf extract, and the mixture thereof (final concentration 50, 100 μg/ml), respectively, was dissolved in distilled water, followed by adding 100 μL of each of the solutions to the A2E solution on the plate.

Further, 100 μL of phosphate buffered saline (PBS) was added to calibrate absorbance of the extract itself, followed by addition of 100 μL of guava leaf extract, banaba leaf extract, and the mixture thereof (final concentration 50, 100 μg/ml), respectively. Then, after measuring absorbance at 430 nm wavelength (A2E absorption wavelength) using an ELISA microplate reader, the solution was irradiated with blue light (4,000 lux) for 30 seconds, 1 minute, 3 minutes, 5 minutes, 8 minutes and 12 minutes, followed by measuring absorbance. After subtracting an inherent absorbance value of each sample from the measured absorbance value, a concentration was calculated using the A2E standard curve.

(2) Result of Experiment

Referring to FIG. 1, it could be confirmed that the control (CTL) including the untreated sample had an amount of unoxidized A2E decreased by about 50% in 1 minute, about 28.5% in 3 minutes, and about 12.5% in 12 minutes, respectively, due to oxidation of A2E relative to irradiation time of blue light. On the other hand, it could be confirmed that the groups treated with the banaba leaf extract, guava leaf extract, and the mixture thereof at concentrations of 50 and 100 μg/ml, respectively, had a tendency to significantly inhibit photooxidation of A2E compared to the control.

Referring to FIG. 1, amounts of unoxidized A2E are in the order of mixture 100>guava leaf 100>mixture 50>guava leaf 50>banaba leaf 100>banaba leaf 50>CTL, wherein each number represents a concentration (μg/ml).

Figure 2:
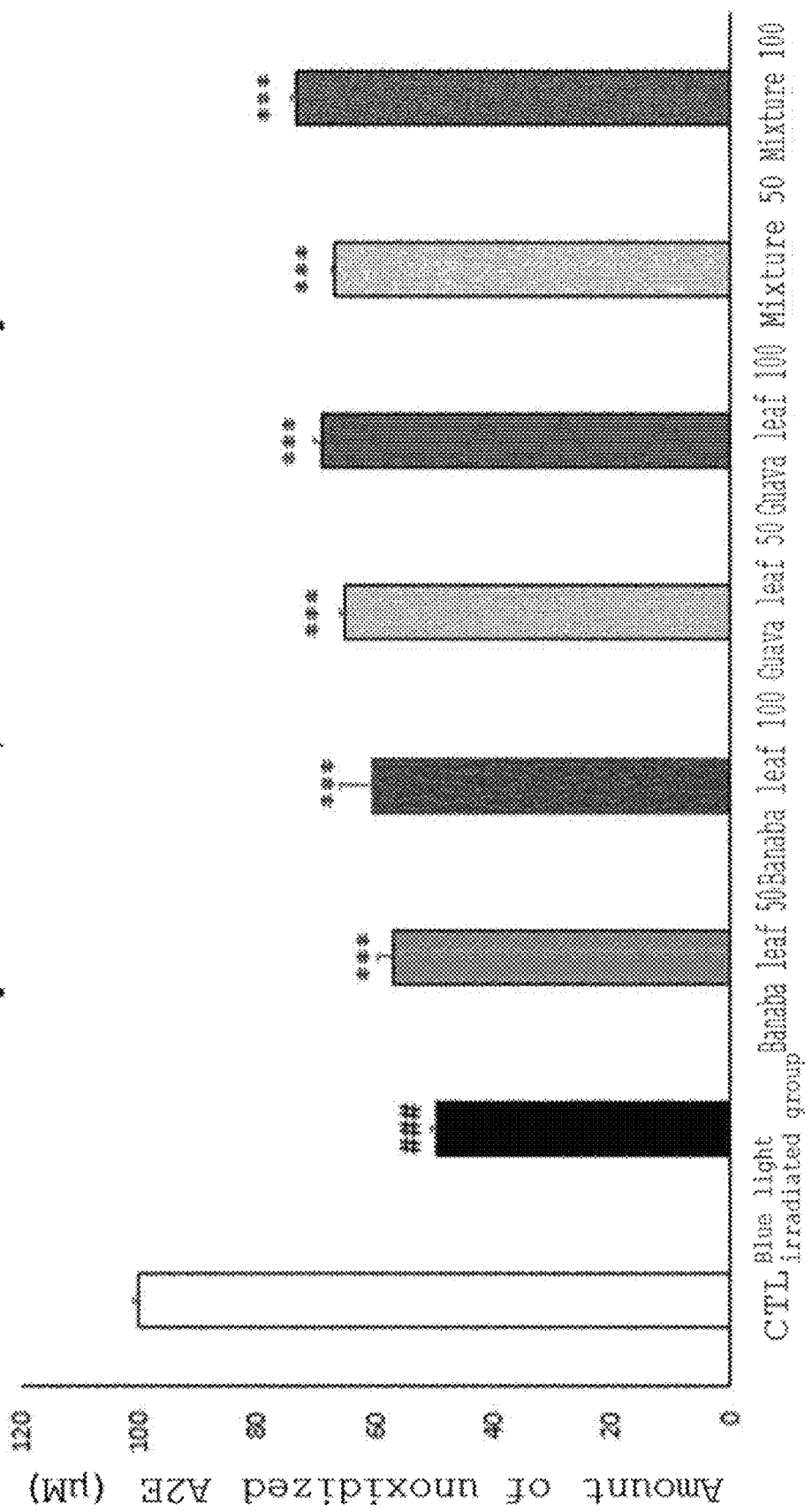
FIG. 2 is a diagram illustrating effects of inhibiting A2E photooxidation due to blue light by guava leaves, banaba leaves and a mixture thereof at a specific time period (3 minutes).

Referring to FIG. 2, when comparing A2E photooxidation protective effect in 1 minute after blue light irradiation, it could be seen that the amount of unoxidized A2E in the blue light irradiated group was reduced by about 50% compared to the control not irradiated with blue light. On the other hand, it could be seen that the groups treated with the banaba leaf, guava leaf, and the mixture thereof at concentrations of 50 and 100 μg/ml, respectively, had reduction of the unoxidized A2E amount by 43%, 39%, 35%, 30%, 33%, 27%, respectively compared to the control.

Example 3. Analysis of Retinal Pigment Epithelial Cell Protective Abilities of Each Extract, and Mixture Thereof Against Blue Light-Induced Photooxidation 1. Analysis of Retinal Pigment Epithelial Cell Protective Abilities of Each Extract and a Mixture Thereof to Blue Light-Induced Photooxidation (1) Experimental Method Since it is already known that photooxidation occurs when retinal pigment epithelial cells accumulated with A2E are irradiated with blue light, it was confirmed whether cytotoxicity derived by irradiation with blue light after 20 μM A2E accumulation in ARPE-19 cells could be suppressed using the banaba leaf extract, guava leaf extract, and the mixture thereof.

Specifically, all ARPE-19 cells were treated with A2E at a concentration of 20 μM for 24 hours, and then treated with 100 μg/mL of the banaba leaf extract, the guava leaf extract, and the mixture thereof in Example 1, respectively, or 17.04 μg/mL (30 μM) of lutein for 24 hours. Thereafter, the treated cells were irradiated with blue light (4,000 lux) for 10 minutes. 24 hours after blue light irradiation, cell viability of ARPE-19 cells was measured by a cell counting kit-8 (Dojindo Labs, Japan), and the percentage of cell viability of each treatment group was compared to the control not irradiated with blue light. Lutein was used as a positive control.

(2) Result of Experiment

Figure 3:
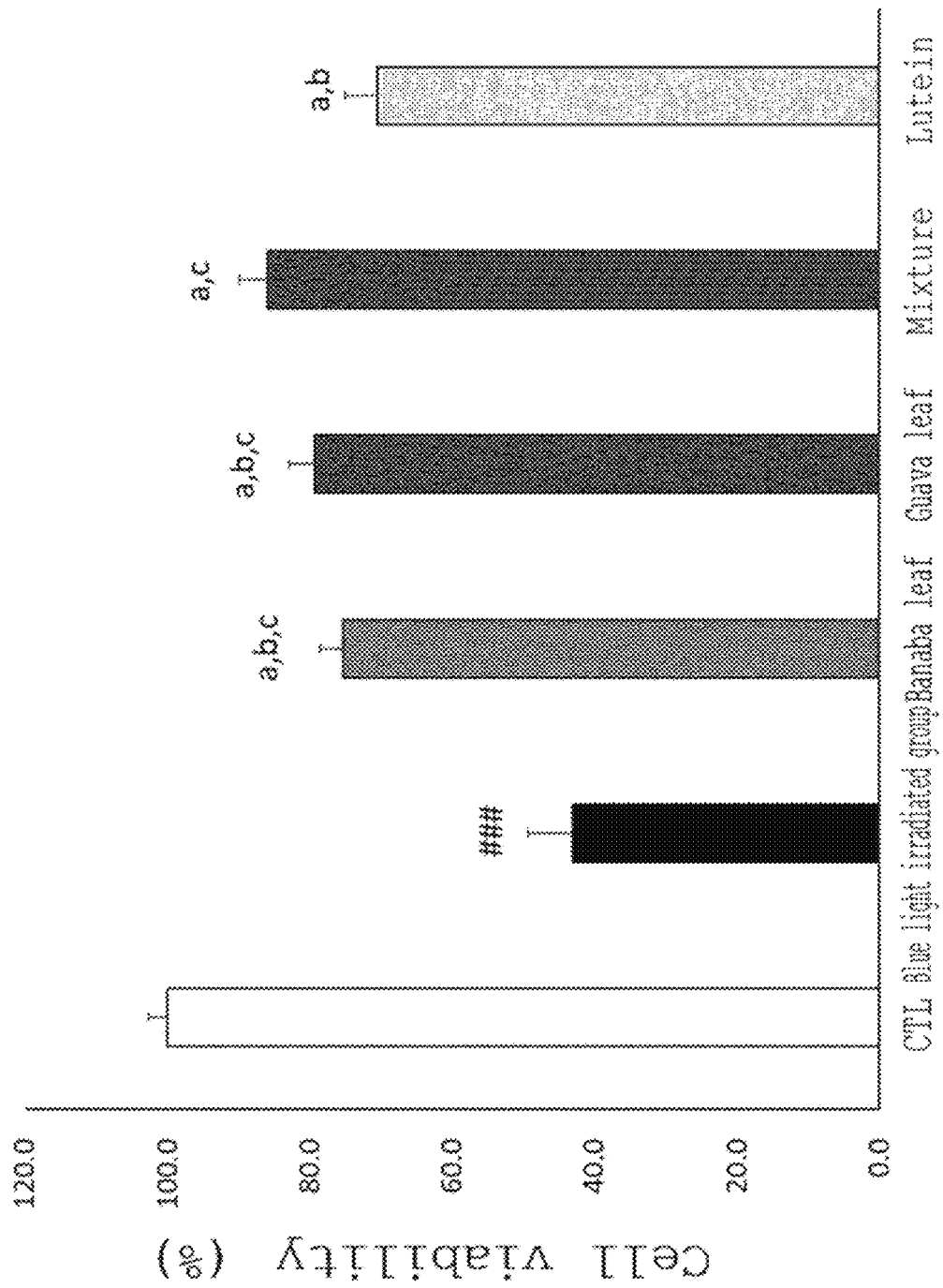
FIG. 3 is a diagram illustrating effects of inhibiting a death of retinal pigment epithelial cells by guava leaves, banaba leaves, a mixture thereof and lutein (###: control (CTL) (P<0.001), a: vs blue light group (P<0.001)), b: vs mixture (P<0.001), c: vs lutein (P<0.05)).

Referring to FIG. 3, it could be seen that cell viability of the blue light irradiated group was significantly reduced (P<0.001) compared to the control not irradiated with blue light, thereby inducing cell death (apoptosis). By setting a difference in cell viability between the control not irradiated with blue light and the blue light irradiated group to be 100%, cell protective effects of each extract were estimated by calculating cell protective effects through a difference in cell viability between the blue light irradiated group and the treated group. As a result, in terms of cell viability, lutein has cell protective effect of 48.4%, while the banaba leaf extract has cell protective effect of 56.7%. Likewise, the guava leaf extract has cell protective effect of 63.6%, while the mixture of the above extracts has cell protective effect of 75.2%. This suggests that the groups treated with the mixture, the guava leaf extract and the banaba leaf extract had better cell protective effects than the lutein 17.04 μg/mL (30 μM) treatment group, and also suggests that the mixture of the guava leaf extract and banaba leaf extract showed more excellent protective effect than the guava leaf extract or the banaba leaf extract alone.

Figure 4:
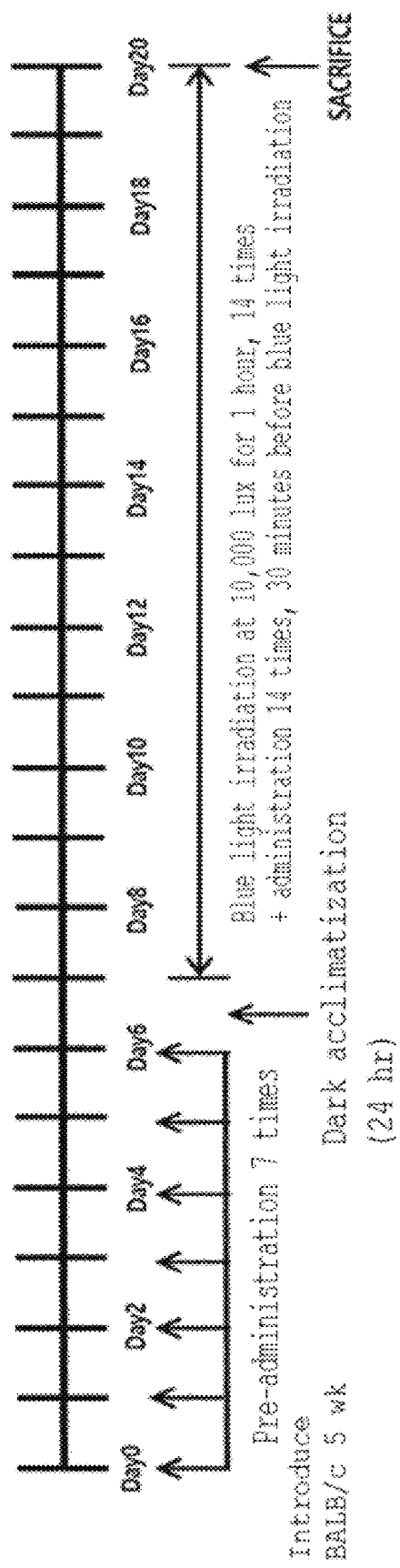
FIG. 4 is a diagram illustrating schedules of animal experiments to confirm effects of preventing and treating macular degeneration by guava leaves, banaba leaves and a mixture thereof.

Example 4. Analysis of Blue Light-Induced Macular Degeneration Inhibitory Ability of Each Extract, and Mixture Thereof 1. Analysis of Blue Light-Induced Macular Degeneration Inhibitory Abilities of Each Extract and a Mixture Thereof (1) Experimental Method Balb-c mice (5 weeks old, males) were acclimated and bred for 2 days, and then orally administered with each of the banaba leaf extract, the guava leaf extract, the mixture thereof or lutein (50 mg/kg) once daily for 7 days. Then, after 24 hours of dark acclimatization, each of the extracts and the mixture and lutein was orally administered for 14 days, and 30 minutes later, followed by blue light irradiation at 10,000 lux for 1 hour per day. 24 hours after the blue light irradiation and the end of administration of the extract, the mice were sacrificed to an extract eyeball, and then, retinal cell protective effects were determined through tissue staining (FIG. 4).

The extracted eyeball tissue was fixed with a neutral buffered formalin solution. The fixed eyeball was washed with running water and was subjected to a dehydration process using alcohol. Thereafter, a clearing process was performed using Xylene, and proper rigidity was given to the tissue using paraffin. The eyeball was made into a predetermined shape of paraffin block, and then cut to 4 μm thickness. The cut eyeball was subjected to hematoxylin & eosin (H & E) staining. After preferential treatment using hematoxylin, the eyeball was left at room temperature for 30 seconds, and the washed with running water for 10 minutes. Thereafter, the eyeball was treated using eosin for 1 minute. The stained organs were observed at a position of 600 to 900 μm away from the optic nerve using a microscope (Olympus Optical, Tokyo, Japan). Then, a thickness of the outer nuclear layer (ONL) of the visual cell was measured by Image J software (National Institute of Health, Starkville, Md., USA)), followed by counting the number of nuclei.

(2) Result of Experiment

Figure 5:
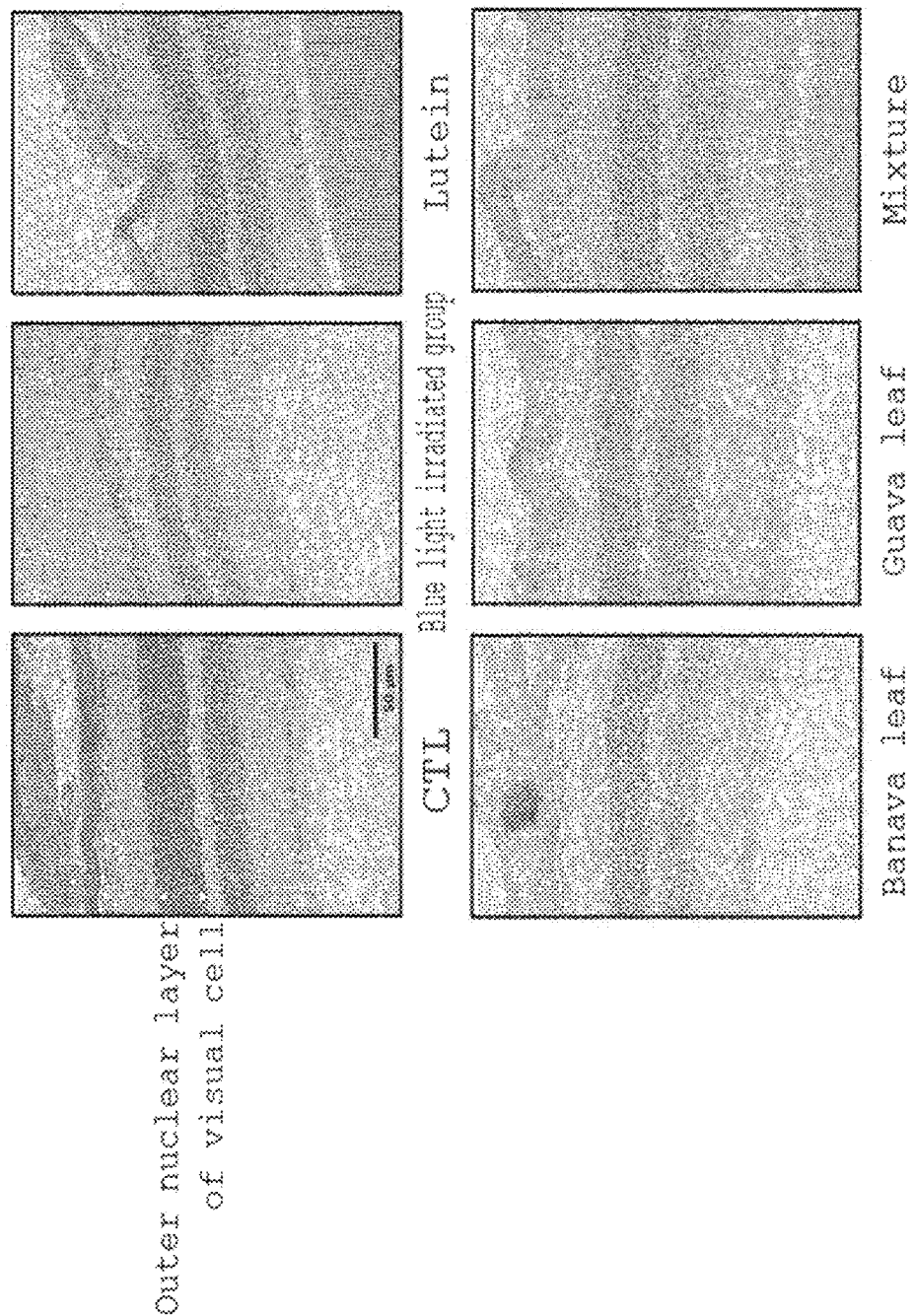
FIG. 5 is a diagram illustrating effects of preventing a damage to outer nuclear layer of a visual cell (ONL) by guava leaves, banaba leaves, a mixture thereof and lutein in an animal model with blue light-induced macular degeneration.
Figure 6:
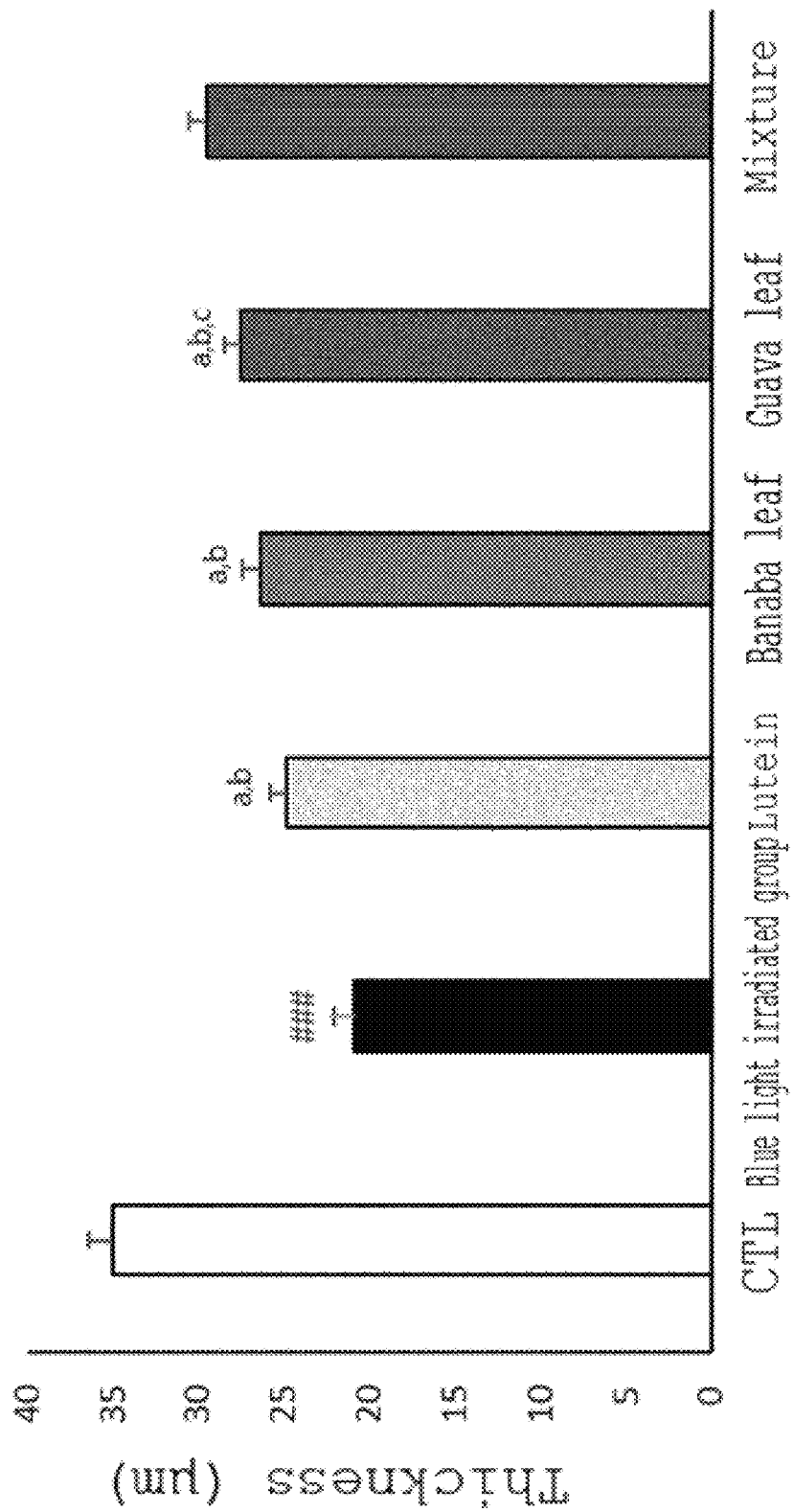
FIG. 6 is a diagram quantitatively illustrating effects of preventing a damage to the outer nuclear layer of a visual cell (ONL) by guava leaves, banaba leaves, a mixture thereof and lutein in an animal model with blue light-induced macular degeneration (###: vs control (P<0.001), a: vs blue light group (P<0.001), b: vs mixture (P<0.01), c: vs lutein (P<0.05)).

Referring to FIGS. 5 and 6, as a result of measuring the thickness of ONL of the visual cell, the ONL thickness in the blue light irradiated group was decreased by 42% compared to the control not irradiated with blue light (P<0.001). It could be seen that the groups administered with the banaba leaf extract, the guava leaf extract, the mixture thereof or lutein, respectively, had significantly increased ONL thickness, compared to the control not irradiated with blue light. By setting a difference in the ONL thickness between the control not irradiated with blue light and the blue light irradiated group to be 100%, ONL thickness protective effects due to blue light in each administration group were estimated by calculating ONL protective effects through a difference in the ONL thickness between the blue light irradiated group and the treated group. As a result, in terms of ONL thickness, it could be seen that the lutein-administered group had ONL protective effect of 28.2%, while the groups administered with the banaba leaf extract, the guava leaf extract, and the mixture thereof showed ONL protective effects of 39.0%, 47.6% and 60.9%, respectively.

In the blue light-induced macular degeneration model, the above results suggest that the banaba leaf extract, the guava leaf extract, and the mixture thereof have effects of significantly repairing retinal cell damage in levels superior to lutein. Further, the above results suggest that the mixture of the banaba leaf extract and the guava leaf extract has better protective effects on retinal cell damage than the banaba leaf extract or the guava leaf extract alone.

The invention claimed is:

1. A method for treating macular degeneration comprising administering to a subject in need thereof a composition comprising an effective amount of a banaba leaf extract.

2. The method of claim 1, wherein the composition further comprises a guava leaf extract.

3. The method of claim 1, wherein the banaba leaf extract is an extract obtained by extracting a banaba leaf with an extraction solvent comprising at least one of water and C1 to C4 alcohol.

4. The method of claim 3, wherein the extraction solvent comprises at least one of methanol and ethanol.

5. The method of claim 1, wherein the composition is a pharmaceutical composition.

6. The method of claim 5, wherein the pharmaceutical composition further comprises a pharmaceutical composition excipient.

7. The method of claim 1, wherein the composition is included in a health functional food.

8. The method of claim 1, wherein the composition comprises an effective amount of the banaba leaf extract for treating macular degeneration.

9. The method of claim 3, wherein the extraction solvent C1 to C4 alcohol.

* * * * *